United States Patent [19]
Durgan et al.

[11] 3,973,429
[45] Aug. 10, 1976

[54] TEST APPARATUS FOR ENGINE HEADS

[75] Inventors: Virgil R. C. Durgan, Tremont; Milton J. Palma, Pekin, both of Ill.

[73] Assignee: Caterpillar Tractor Co., Peoria, Ill.

[22] Filed: July 14, 1975

[21] Appl. No.: 595,649

[52] U.S. Cl. .............................................. 73/49.7
[51] Int. Cl.[2] ...................................... G01M 15/00
[58] Field of Search ................ 73/118, 119 R, 49.7, 73/49.8; 137/557

[56] References Cited
UNITED STATES PATENTS

| | | | |
|---|---|---|---|
| 3,360,984 | 1/1968 | Salsbury | 73/49.7 |
| 3,452,591 | 7/1969 | Phillips et al. | 73/118 |
| 3,608,369 | 9/1971 | Wilkinson | 73/49.7 X |

*Primary Examiner*—Jerry W. Myracle
*Attorney, Agent, or Firm*—Wegner, Stellman, McCord, Wiles & Wood

[57] ABSTRACT

Apparatus for testing engine heads of internal combustion engines of various sizes for fluid tightness of internal cavities in a head which commmunicate with ports in the fire deck surface of the head. A universal mounting frame for a cylinder head is rotatable on a longitudinal pivot axis to position the head with its fire deck surface at any orientation relative to the axis. Longitudinal support rails are positioned above the water ports, and spring loaded stopper means and fluid supply and venting members which are longitudinally adjustable on the rails are aligned with the ports, and the support rails are then moved down to seal the stoppers and heads against the rims of the ports. Compressed air, and then hot water are introduced to the head cavities to check it for leaks.

26 Claims, 5 Drawing Figures

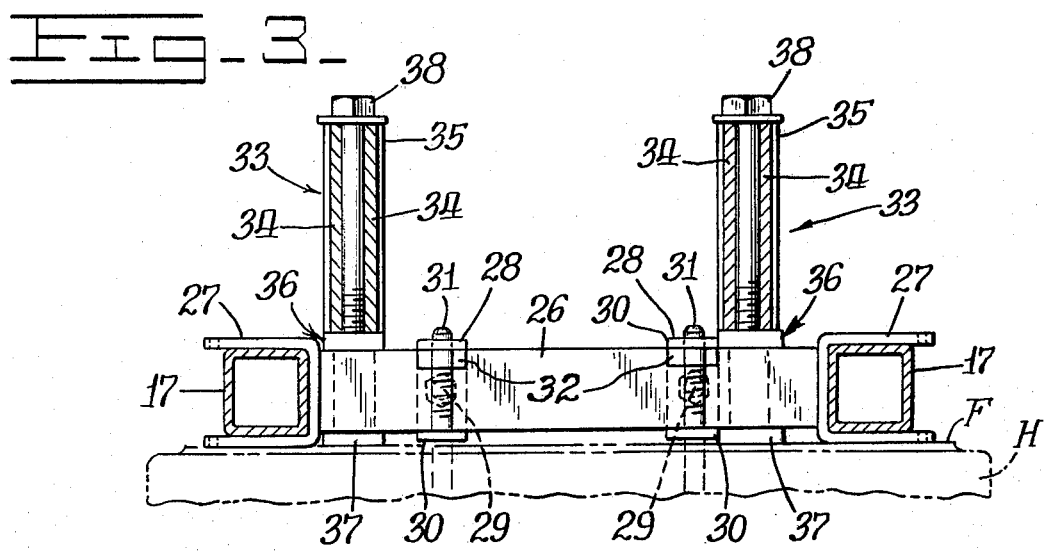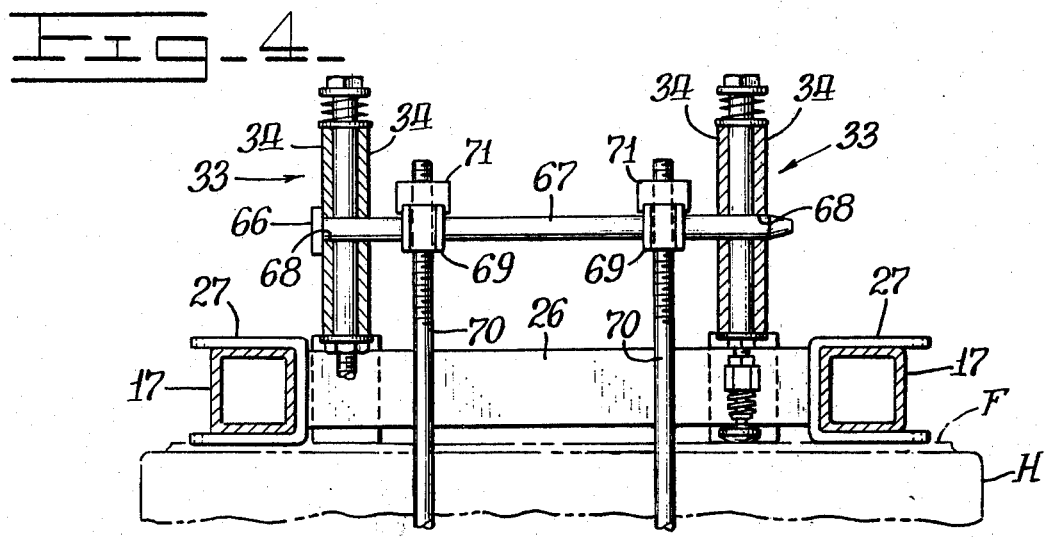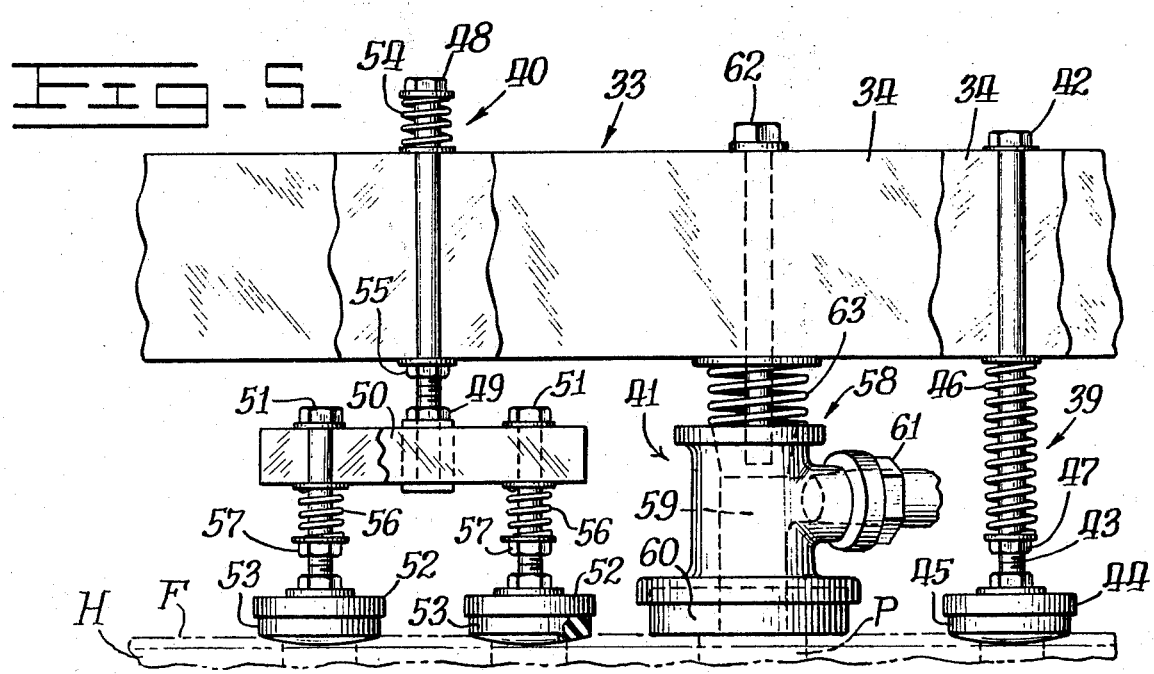

TEST APPARATUS FOR ENGINE HEADS

BACKGROUND OF THE INVENTION

The engine heads of internal combustion engines, and particularly of large diesel engines, are extremely complex structures which have numerous internal coolant, air, or fuel mixture passages, and also intake and exhaust valve and fuel injector ports which are required for proper combustion and containment of the hot, high pressure gases. Seals about the fuel injectors and complementing precombustion chambers may leak, and cracks may develop in the walls which separate the many internal cavities; and if this occurs a detrimental intermixing of coolant fluid, gas, fuel, antifreeze, lubricating oil and other additives can occur. Regularly scheduled spectrophotometer analysis of oil samples from such engines indicates the seriousness of leakage and when engine repairs are in order but, even when this is known, the leaks are very difficult to locate.

The engine head must be removed from the engine, the ports which connect the internal coolant cavities with the related cavities in the engine block must be plugged, and either compressed air or water under pressure must then be introduced to the coolant cavity in an attempt to locate any cracks or leaks between the coolant cavity and any of the other cavities or passages in the engine head.

Engine heads come in many different sizes and with numerous different patterns of cavities, passages and ports; so sealing all the necessary ports and openings requires a variety of plates, plugs, etc.

The problem of locating leaks and cracks is compounded by the fact that some leaks show up only when the coolant cavity is filled with water or other coolant at relatively high temperature and a pressure comparable to that at which the system operates in service. It is both difficult and dangerous to initially locate leaks and cracks by means of hot water under pressure, because a bad crack can spray scalding water around the test area. Thus, it is desirable to proceed as far as possible with compressed air, repair all leaks and cracks which are located by the use of compressed air, and then give the engine head a final test at relatively high temperature and with water under pressure.

SUMMARY OF THE INVENTION

The principal object of the present invention is to provide apparatus which accommodates engine heads of a wide variety of sizes and types, and which simplifies the preparation for and testing of an engine head.

Another object of the invention is to provide an apparatus in which the mounting frame is rotatable on a longitudinal pivot axis and may be locked in any of a number of positions relative to the pivot axis to facilitate mounting an engine head on the frame, sealing the head, testing it with compressed air, locating leaks and cracks, and repairing them.

Yet another object of the invention is to provide apparatus which facilitates the connection of pressure hoses to selected ports and the sealing of other ports.

Still another object of the invention is to provide apparatus which greatly simplifies and facilitates carrying out the successive steps of mounting the engine head, attaching pressure hoses and sealing it, testing with compressed air for audible location of cracks and leaks, including the use of supersonic sound detectors, the repair of all leaks and cracks located by the compressed air testing, heating the head and testing it with hot water under pressure, and cooling the head for final repair and removal from the apparatus.

THE DRAWINGS

FIG. 3 is a fragmentary sectional view taken substantially as indicated along the line III—III of FIG. 2;

FIG. 4 is a fragmentary sectional view taken substantially as indicated along the line IV—IV of FIG. 2; and FIG. 5 is a fragmentary side elevational view on an enlarged scale with parts broken away and parts in section to illustrate different types of stopper means and a quick attachment fluid coupling means.

DETAILED DESCRIPTION OF THE INVENTION

Figure 1:
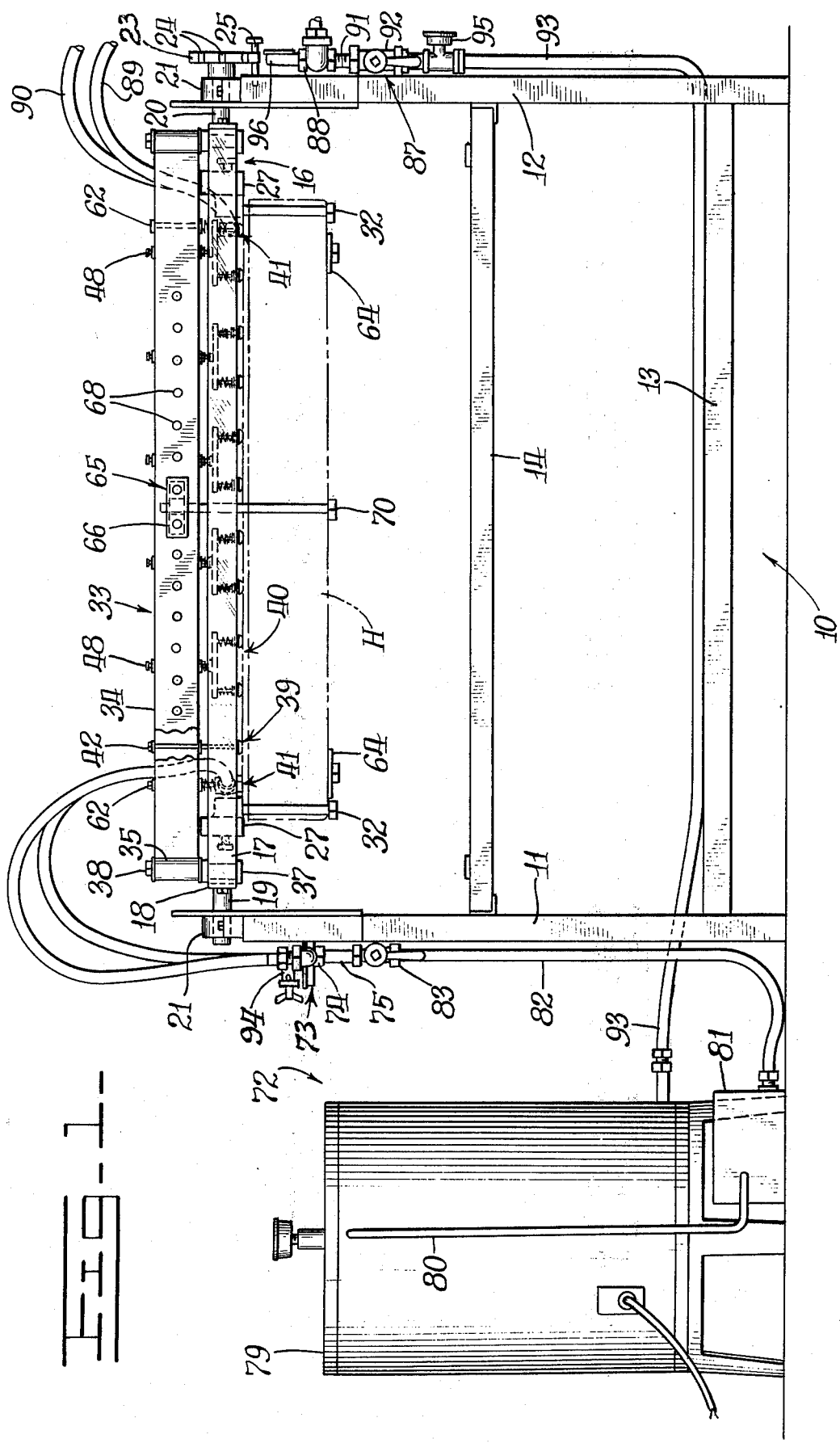
FIG. 1 is a side elevational view of the apparatus of the invention with an engine head which is mounted therein and sealed for testing illustrated in broken lines.
Figure 2:
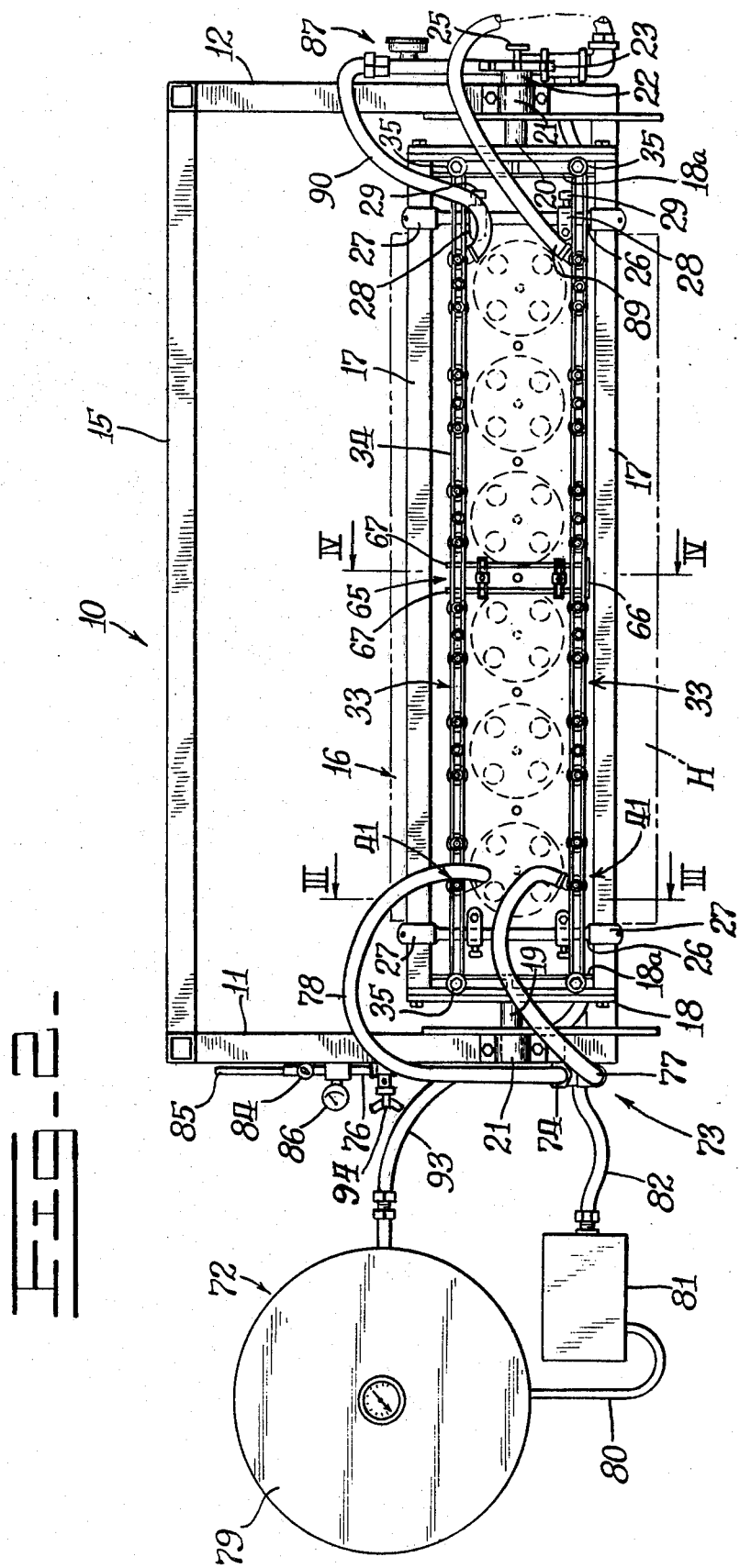
FIG. 2 is a plan view of the apparatus with an engine head shown in broken lines.

Referring to FIGS. 1 and 2, the apparatus of the present invention includes a base, indicated generally at 10, with rectangular end frames 11 and 12 that are connected by a longitudinal lower frame member 13, a shelf 14, and a top rear frame member 15. If desired, a table top may be mounted on the member 15 and the rearward portions of the rectangular end frames 11 and 12.

A rectangular engine head mounting frame, indicated generally at 16, has elongated, parallel side beams 17 connected by end plates 18. Extending longitudinally from the end plates are coaxial spindles 19 and 20 which are journalled in bearing blocks 21 that surmount the forward portions of the end frames 11 and 12. The spindle 20 projects outside the supporting bearing block 21 and has a bushing 22 and locking disc 23 that is provided with peripheral slots 24 which are engaged by an axially movable locking bolt 25. Thus, the mounting frame 16 may occupy a horizontal position as illustrated, or an inverted horizontal position, or a vertical position, or positions inclined at 45°.

The mounting frame 16 is at least as long as the largest motor head to be mounted thereon, and the distance between the side beams 17 is greater than the maximun space between the coolant bores which flank the cylinder openings of an engine head. A pair of transverse mounting bars 26 is provided with outwardly open, fixed jaws 27 which embrace the longitudinal frame beams 17, so that the mounting bars 26 may be slid to any desired positions along the beams 17. As best seen in FIG. 3, each of the mounting bars 26 carries a pair of bracket means 28 which are slidable on the mounting bars so as to adjust their distances from one another and from the longitudinal frame beams 17; and each of the bracket means 28 has a locking screw 29 by which it may be fixed in any desired position upon the mounting bar. The mounting bracket means 28 have flanges 30 provided with aligned holes to receive long, headed mounting bolts 31 which extend through bores in a motor head H and are threaded into nuts 32 formed integrally with brackets 28.

To mount a motor head H upon the mounting frame 16, the latter is first oriented in a horizontal position inverted from the position which is illustrated, and the mounting bars 26 and bracket means 28 are positioned so that the aligned holes in the bracket means will be in register with a motor head H which is then laid on top of the mounting frame 16 with its fire deck surface F down where it rests upon the upper flanges of the fixed jaw 27. The bolts 31 are then positioned impaling the flanges of the bracket means and the registering holes in the motor head, so the nuts 32 and bolts may be secured. The locking bolt 25 is then removed, the mounting frame 16 is returned to the position illustrated in the drawings with the fire deck F uppermost, and the unit is again locked in place by inserting the locking bolt 25.

The apparatus also includes a pair of longitudinally extending, parallel support rails which are indicated generally at 33. Each of the support rails 33 consists of a pair of closely spaced, parallel plates 34 which have their ends welded to hollow bosses 35. As best seen in FIG. 1 to 3, the hollow bosses 35 attach to members 36 which extend between closely spaced plates, one of which is the mounting frame end plate 18 and the other of which is a parallel plate 18a. As best seen in FIG. 3, members 36 have external flanges 37 which rest upon the plates 18 and 18a so that the support rails 33 may be laterally adjusted to position them above ports P (FIG. 5) which extend from the fire deck surface F of the engine head H into communication with the internal coolant cavities in the head. Threaded bosses between the plates 18 and 18a receive long headed bolts 38 by means of which the support rails are secured in place.

As best seen in FIG. 5, the support rails 33 carry two different kinds of spring loaded stopper means, indicated generally at 39 and 40, respectively, and spring loaded, quick attachment fluid coupling means, indicated generally at 41. The stopper means 39 includes a long, headed bolt 42 which provides an upright mounting stem that hangs upon the two spaced plates 34 that constitute the support rails, and a threaded lower end portion 43 of the bolt receives a stopper member 44 that has a resilient sealing pad 45 bonded to its lower surface. A compression spring 46 surrounds the stem and is confined between the support rail 33 and an adjusting nut 47.

The stopper means 40 includes an elongated bolt 48 which extends between the plates 34 and has a threaded fitting 49 at its lower end which is provided with a bifurcated cross arm 50 at the ends of which are headed bolts 51, and at the lower end of each of the bolts 51 is a stopper member 52 which includes a sealing pad 53 bonded to its lower surface. A compression spring 54 between the head of the bolt 48 and the support rail 33 cooperates with a nut 55 to adjustably support the bolt 48 in the support rail 33; and compression springs 56 surrounding the bolts 51 are confined between the cross arm 50 and adjusting nuts 57.

The quick attachment fluid coupling means 41 includes a body, indicated generally at 58, which conveniently is a T coupling which has had its upper end plugged so that it has an internal passage 59 one end of which is surrounded by an annular fluid seal 60 that is adapted to bear upon the fire deck surface surrounding a port P, and the other end of which is connected by a nipple 61. Surmounting the body 58 is an upright mounting stem 62 in the form of a headed bolt which hangs upon the spaced elements 34 of the support rail 33 and has its lower end screwed into the plug in the top of the coupling body 58. A compression spring 63 is confined between the top of the body 58 and the under side of the support rail 33.

After the support rails 33 are aligned with the ports P, the necessary number of spring loaded stopper means 39 or 40 are positioned in alignment with all but the end ones of the ports P on each side of the engine head H, and the quick attachment coupling means are positioned in alignment with the end ports on each side of the head. The sealing pads 45, 53 and 60 are adjusted to be lightly in contact with the fire deck surface F, and the bolts 38 are then tightened to move the support rails 33 downwardly and push the entire arrays of stoppers and fluid couplings into sealing engagement with the fire deck surface at the rims of the ports.

There are other openings into the engine head which cannot be conveniently sealed by the use of the array of spring loaded stopper means on the support rails 33; and these may be closed, where required, by auxiliary sealing plates 64 (FIG. 1) and small diameter, expandable rubber stoppers (not shown) of a known type.

In some situations, particularly with large and heavy engine heads that are to be tested under relatively high pressure, it is desirable to use auxiliary, intermediate head support means, indicated generally at 65, the structure of which is best illustrated in FIG. 4. A plate 66 has a pair of spaced studs 67 which are arranged to impale a pair of adjacent, aligned sets of mounting holes 68 which are formed in the plates 34 that comprise the support rails 33. The studs 67 carry a pair of slidable brackets 69 that receive long threaded bolts 70 which screw into captive nuts 71 associated with the brackets 69.

Referring again particularly to FIGS. 1 and 2, the apparatus includes a fluid supply system, indicated generally at 72. Mounted on the base end member 11 is a plumbing fitting, indicated generally at 73, which includes a cruciform coupling 74 which has a water inlet pipe 75 communicating with its lower end and a compressed air supply pipe 76 communicating with one side. A pressure conduit 77 and a pressure conduit 78 are connected to the other two nipples of the coupling 74, and each of the conduits 77 and 78 makes a fluid tight connection with one of the two quick attachment coupling means 41 as seen in FIG. 2.

The fluid supply system also includes a water heater 79 from which hot water may be drawn through a pipe 80 by a pump 81 which delivers it through a pressure conduit 82 to a manual globe valve 83 which permits control of the flow of water through the pressure conduits 77 and 78.

The air line 76 is connected through a manual valve 84 with a pipe 85 that leads to a compressed air source, and an air pressure gauge 86 completes the fluid supply system.

Mounted on the base end frame 12 is a plumbing system, indicated generally at 87, for the venting of fluid from the motor head H. The plumbing system 87 includes a cruciform coupling 88, and connected to two of the ports of the coupling 88 are venting pressure conduits 89 and 90 which are connected to the other two quick attachment couplings 41; while attached to a third port of the coupling 88 is a water pipe 91 which leads through a manual valve 92 to a return hose 93 (FIG. 1) by means of which water is returned to the heater 79. The fourth port of the coupling 88 can accomodate other instruments. A high pressure air vent valve 94 preferably is placed near supply valve 84.

After an engine head H has been mounted and sealed as heretofore described, the air inlet valve 84 is opened with the water inlet valve 83 and the water and air vent valves 92 and 94 closed, and the head is put under the predetermined air pressure such, for example, as 50 p.s.i. Cracks or leaks in the head which are of a type to permit an audible flow of air through them may then be noted by listening. Less severe air leaks may then be located by using a commercially available ultra sonic sound detector which is a manual, hand held implement that is connected to a set of earphones.

All cracks and leaks which are located are then repaired, and water inlet valve 83 and the water venting valve 92 are both opened, and the pump 81 is started to circulate water at about 180° through the engine head until appropriately located temperature sensing devices, including a thermometer 95 at the venting coupling 88, indicate that the motor head has reached a desired high temperature close to 180°. The water inlet valve 83 and the water venting valve 92 are then closed, and the air inlet valve 84 is opened to pressurize the hot water in the engine head to successively higher pressure beginning at approximately 15 p.s.i. and ending at about 50 p.s.i. Any cracks or leaks which develop under the pressurized hot water test are marked, and the water in the engine head is vented by opening the water venting valve 92 and forcing out the water with low pressure air. Air flow is continued to dry the interior cavities and passages of the engine head and to cool it; and when the temperature sensing means, and in particular an engine head surface temperature sensor 96 near the venting lines, indicate that the head is cool enough to handle the support rails 33 are removed, the mounting frame 16 is returned to its original position with the engine head uppermost, and the bolts are removed to permit the engine head to be lifted off the mounting frame.

The foregoing detailed description is given for clearness of understanding only and no unnecessary limitations should be understood therefrom, as modifications will be obvious to those skilled in the art.

We claim:

1. In apparatus for testing engine heads of internal combustion engines of various sizes for fluid tightness of internal cavities in a head which communicate with ports in the fire deck surface of the head, said apparatus including first flexible conduit means for supplying fluid from a pressurized fluid source to said cavities through certain ones of said ports and second flexible conduit means for venting fluid from said cavities through certain others of said ports, the improvement comprising, in combination:

a base;

a rectangular mounting frame on said base which has narrow end plates and long side beams, said frame being at least as long as the largest head to be mounted thereon;

means for detachably mounting a head of any of various sizes on said mounting frame with the fire deck surface uppermost;

a pair of longitudinally extending, substantially parallel support rails;

means mounting said support rails on said mounting frame above and in alignment with the fire deck surface;

a plurality of stopper means each of which includes an upright mounting stem with a resilient stopper at its lower end;

at least two, quick attachment fluid coupling means, each of said coupling means including a body with a fluid passage therethrough, an annular fluid seal surrounding one end of said passage and adapted to bear upon the fire deck surface surrounding one of said certain ports, means at the other end of the passage for fluid tight attachment of one of the flexible conduit means, and an upright mounting stem surmounting said body;

means for securing each of said mounting stems in a depending position on one of said support rails at any desired location between the ends of the rails, so that each stopper means and each coupling means is aligned with one of the ports in the fire deck surface;

and means for forcing each of said stopper means and coupling means resiliently downwardly into sealing engagement with the fire deck surface at the rim of the port with which it is aligned.

2. The improvement of claim 1 which includes means supporting the mounting frame on the base for rotation about a longitudinal horizontal axis, and manually releasable locking means for locking said frame in various orientations about said axis.

3. The improvement of claim 1 in which the means for detachably mounting a head on the mounting frame includes a plurality of mounting bars which span the width of the frame and which may occupy various positions along the frame, and bracket means mounted on each bar for movement normal to the sides of the supporting frame.

4. The combination of claim 3 which includes mounting bolts that impale the bracket means and that also impale bolt holes through the head.

5. The improvement of claim 3 in which the mounting frame has unobstructed side beams and the mounting bars have open jaws at both ends which slidably engage said side beams.

6. The improvement of claim 3 which includes means supporting the mounting frame on the base for rotation about a longitudinal horizontal axis, and manually releasable locking means for locking said frame in various orientations about said axis.

7. The improvement of claim 1 which includes means mounting the support rails for lateral adjustment between the side beams of the mounting frame.

8. The improvement of claim 7 in which the mounting means for the support rails are slidably supported on the end plates of the mounting frame.

9. The improvement of claim 8 in which each end plate comprises parallel members, and the mounting means include upright hollow bosses which extend between said members and have flanges above and below the members, and threaded bolts inpaling the bosses and engaging internal threads in the flanges below the members.

10. The improvement of claim 7 in which the support rails are unobstructed, and the upright mounting stems include means slidably engaging said rails for movement of said stems along said rails.

11. The improvement of claim 10 in which each support rail consists of parallel bars and the mounting stems extend between said bars and have enlarged heads overlying both bars.

12. The improvement of claim 1 in which the support rails are unobstructed, and the upright mounting stems include means slidably engaging said rails for movement of said stems along said rails.

13. The improvement of claim 12 in which each support rail consists of parallel bars and the mounting stems extend between said bars and have enlarged heads overlying both bars.

14. The improvement of claim 12 which includes means mounting the support rails for lateral adjustment between the side beams of the mounting frame.

15. The improvement of claim 14 in which the mounting means for the support rails are slidably supported on the end plates of the mounting frame.

16. The improvement of claim 1 which includes intermediate head support means comprising a cross stud mounted on the support rails, brackets which are laterally adjustable on said stud, and elongated bolts impaling said brackets and also impaling holes in a head.

17. The improvement of claim 16 which includes means for mounting the cross stud at various positions along the support rails.

18. The improvement of claim 17 in which said means for mounting the cross stud comprises a series of aligned holes along the support rails, any of which aligned holes may be impaled by said stud.

19. The improvement of claim 1 in which the stopper means includes a rotatable cross arm at the lower end of the stem, a suspension bolt at each end of the cross arm, a stopper at the bottom of each bolt, and a compression spring surrounding each bolt between the cross arm and the stopper.

20. The improvement of claim 19 in which the stem has an enlarged head by means of which it is suspended on a support rail, and a compression spring is positioned between said head and the support rail.

21. The improvement of claim 1 in which the upright stem of the stopper means has an enlarged head by means of which it is suspended on a support rail, the stopper is spaced below the support rail, and a compression spring surrounds the stem between the stopper and the support rail.

22. The improvement of claim 1 which includes means for moving each support rail toward the head to force the stopper means and the coupling means downwardly.

23. The improvement of claim 1 which includes a fluid supply fitting communicating with the first flexible conduit means, a compressed air supply line to said fluid fitting, a pressurized hot water supply line from a source of hot water to said fluid fitting, and valve means for selectively admitting compressed air or pressurized hot water to said fitting and said first flexible conduit.

24. The improvement of claim 23 which includes a fluid venting fitting communicating with the second flexible conduit means, a hot water return line from said venting fitting to the source of hot water, a valve for controlling flow of fluid through said return line, an air venting port in said venting fitting, and a valve for controlling the venting of air from said venting fitting.

25. In apparatus for testing engine heads of internal combustion engines of various sizes for fluid tightness of internal cavities in a head which communicate with ports in the fire deck surface of the head, said apparatus including first flexible conduit means for supplying fluid from a pressurized fluid source of said cavities through certain ones of said ports and second flexible conduit means for venting fluid from said cavities through certain others of said ports, the improvement comprising, in combination:
 a base;
 a rectangular mounting frame on said base which has narrow end plates and long side beams, said frame being at least as long as the largest head to be mounted thereon;
 means for detachably mounting a head of any of various sizes on said mounting frame with the fire deck surface uppermost;
 means for sealing the ports in the fire deck surface of the head;
 fluid coupling means for placing a flexible fluid supply conduit means in communication with one certain port;
 fluid coupling means for placing a flexible fluid venting conduit means in communication with another certain port, so that fluid may be circulated through said one certain port, through an internal coolant cavity, and out of said another certain port;
 a fluid supply fitting communicating with said fluid supply conduit;
 a compressed air supply line to said fluid supply fitting;
 a hot water supply line to said fluid supply fitting;
 an air valve to control flow of air to said fluid supply fitting;
 a water valve to control flow of hot water to said fluid supply fitting;
 a fluid venting fitting communicating with said fluid venting conduit;
 an air venting valve to control venting of air through said fluid venting fitting;
 and a water venting valve to control venting of water through said fluid venting fitting.

26. In apparatus for testing engine heads of internal combustion engines of various sizes for fluid tightness of internal cavities in a head which communicate with ports in the fire deck surface of the head, said apparatus including first flexible conduit means for supplying fluid from a pressurized fluid source to said cavities through certain ones of said ports and second flexible conduit means for venting fluid from said cavities through certain others of said ports, the improvement comprising, in combination:
 a base;
 a rectangular mounting frame on said base which has narrow end plates and long side beams, said frame being at least as long as the largest head to be mounted thereon;
 means for detachably mounting a head of any of various sizes on said mounting frame;
 coaxial spindles at the ends of the said mounting frame upon which the frame is rotatable about a horizontal axis;
 and manually releasable locking means for selectively locking the mounting frame in a horizontal position and in several other angular orientations about said axis.

* * * * *